United States Patent [19]

Khek

[11] Patent Number: 5,151,084
[45] Date of Patent: Sep. 29, 1992

[54] ULTRASONIC NEEDLE WITH SLEEVE THAT INCLUDES A BAFFLE

[75] Inventor: Sokhuom Khek, Chicago, Ill.

[73] Assignee: Fibra-Sonics, Inc., Chicago, Ill.

[21] Appl. No.: 737,424

[22] Filed: Jul. 29, 1991

[51] Int. Cl.$^5$ .................... A61B 17/00; A61M 1/00
[52] U.S. Cl. .................... 604/22; 128/24 AA; 606/107; 606/169; 604/902; 604/19
[58] Field of Search ............ 604/19, 22, 48, 54; 606/107, 166, 169, 170, 171; 128/43, 35, 305, 24 AA, 749-754

[56] References Cited

U.S. PATENT DOCUMENTS

| | | | |
|---|---|---|---|
| 3,526,219 | 9/1970 | Balamuth | 128/24 AA |
| 3,805,787 | 4/1974 | Banko | 606/169 |
| 4,320,761 | 3/1982 | Haddad | 604/22 |
| 4,681,561 | 7/1987 | Hood et al. | 604/22 |
| 4,741,731 | 5/1988 | Starck et al. | |
| 4,816,017 | 3/1989 | Hood et al. | 604/22 |
| 4,816,018 | 3/1989 | Parisi | 128/24 AA |
| 5,038,756 | 8/1991 | Kepley | 128/24 AA |

Primary Examiner—Stephen C. Pellgrino
Assistant Examiner—Glenn K. Dawson
Attorney, Agent, or Firm—Hill, Van Santen, Steadman & Simpson

[57] ABSTRACT

A baffle with holes formed therein is mounted in a sleeve which surrounds the needle of an ultrasonic handpiece so as to reduce bubbles in the irrigation fluid supplied to the handpiece and thus improve the visibility at the operating site. As irrigation fluid is supplied to the handpiece, it contacts the ultrasonic motor which tends to cause bubbles and by providing the baffle with openings, the bubbles are restricted from passing the baffle and obstructing the vision of the surgeon using the ultrasonic handpiece.

1 Claim, 1 Drawing Sheet

ULTRASONIC NEEDLE WITH SLEEVE THAT INCLUDES A BAFFLE

CROSS-REFERENCES TO RELATED APPLICATIONS

The application entitled "Apparatus For Eliminating Air Bubbles" in which the inventor is Robert H. Pichler, U.S. Ser. No. 737,425 assigned to the assignee of the present application.

BACKGROUND OF THE INVENTION

1. Field of the Invention

This invention relates in general to ultrasonic surgical tools and in particular to a novel apparatus that includes a sleeve with a baffle so as to eliminate bubbles.

2. Description of Related Art

U.S. Pat. No. 4,741,731 assigned to the assignee of the present application discloses an ultrasonic handpiece which provides for irrigation and aspiration at an operating site. The prior art ultrasonic handpieces at times result in bubbles being formed at the operating site which obstructs the surgeon's vision.

SUMMARY OF THE INVENTION

It is an object of the present invention to provide an ultrasonic handpiece with irrigation which includes a sleeve that surrounds the operating needle. Irrigating fluid is supplied between the inside surface of the sleeve and the needle and a baffle is mounted in the sleeve so as to eliminate bubbles from being produced at the operating site.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DETAILED DESCRIPTION OF THE PREFERRED EMBODIMENTS

Figure 1:
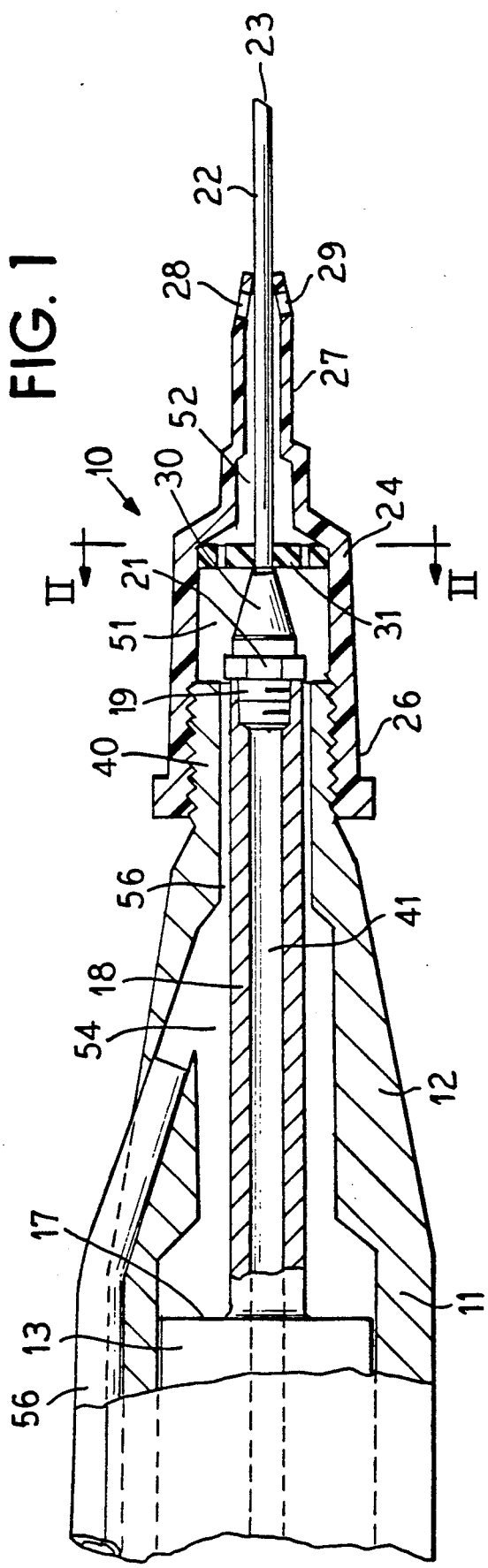
FIG. 1 is a partially cut-away sectional view of the invention.

FIG. 1 illustrates a partial view of an ultrasonic handpiece 10 which has an outer cylindrical case 11 and a conical portion 12 at one end thereof. Ultrasonic motor 13 is mounted within cylindrical portion 11. An extending tubular portion 18 of the motor 13 is formed with a central opening 41 and has an internally threaded portion 19 which threadedly receives a threaded portion 21 of an operating needle 22. A conical portion 30 is formed in the needle 22 between the threaded end 21 and the main body portion of the needle. The needle 22 is formed with a central aspirating opening 23 which communicates with the aspirating passage 41 that extends through member 18 and the handpiece 10. The conical portion 12 has a cylindrical body portion 40 which has external threads upon which a sleeve 24 is received. The sleeve 24 may be made of a suitable plastic and has a threaded portion 26 which mates with the threads on the portion 40 as shown.

Figure 2:
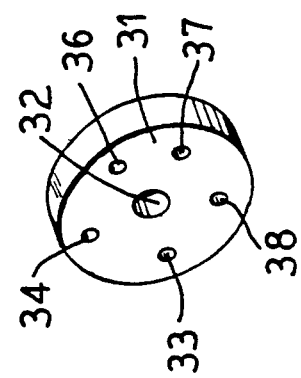
FIG. 2 is a sectional view taken on line II—II of FIG. 1.
Figure 3:
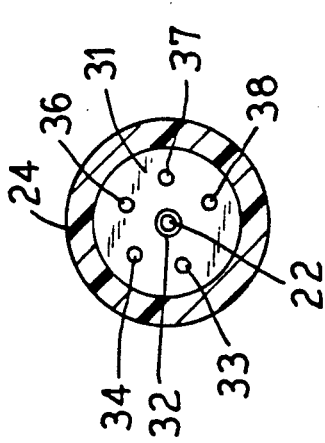
FIG. 3 is an enlarged view of the baffle.

A baffle 31 is mounted in the sleeve 24 and is formed with a central opening 32 through which the needle 22 extends. A plurality of openings 33, 34, 36, 37 and 38 are formed through the baffle 31 as best shown in FIGS. 2 and 3 so as to allow irrigating fluid to pass from the cavity 51 through the baffle 31 into the cavity 52 to the right of the baffle relative to FIG. 1 through portion 27 of the sleeve and out openings 28 and 29 formed in the end 53 of the portion 27. An irrigating tube 56 is connected to the handpiece 10 and supplies irrigating fluid into the cavity 54 which passes through the opening 56 into the opening 51 and then through the baffle 31.

The ultrasonic motor has a shoulder 17 which tends to generate bubbles in the irrigating fluid in the chamber 51 and the openings 33, 34, 36, 37 and 38 of the baffle 31 restrict the bubbles and prevent them from passing through the chamber 52 and through openings 28 and 29 to the operating site. Thus, the baffle 31 results in an improved ultrasonic handpiece in that substantially fewer bubbles are produced using the sleeve 24 with the baffle 31 as compared to prior art ultrasonic handpieces.

Although the invention has been described with respect to preferred embodiments, it is not to be so limited as changes and modifications can be made which are within the full intended scope of the invention as defined by the appended claims.

I claim as my invention:

1. An ultrasonic handpiece for performing operations comprising, an ultrasonic motor mounted in said handpiece, a tubular portion extending from said ultrasonic motor, a hollow needle attached to an end of said tubular portion, a conical portion of said ultrasonic handpiece extending around said tubular portion and a first cavity formed therebetween, an irrigating tube connected to said conical portion and supplying irrigating fluid to said first cavity, a flexible sleeve connected to an end of said conical portion and extending around said needle, a second cavity formed between said sleeve and said needle and fluidly connected to said first cavity, a planar baffle mounted in and across said sleeve and formed with a plurality of equally spaced openings which extend in a direction parallel to said needle, a third cavity formed between said sleeve and said needle and said second and third cavities in fluid communication through said plurality of said openings in said planar baffle, and an outlet opening formed in said sleeve and in fluid communication with said third cavity, said planar baffle mounted so that its plane extends in a direction which is 90 degrees to said needle, wherein suction is applied to said tubular portion for aspiration, and wherein a shoulder is formed at the junction of said tubular portion and said ultrasonic motor.

* * * * *